(12) United States Patent
Sommer et al.

(10) Patent No.: US 6,313,423 B1
(45) Date of Patent: Nov. 6, 2001

(54) APPLICATION OF RAMAN SPECTROSCOPY TO IDENTIFICATION AND SORTING OF POST-CONSUMER PLASTICS FOR RECYCLING

(75) Inventors: Edward J. Sommer, Nashville; John T. Rich, Lebanon, both of TN (US)

(73) Assignee: National Recovery Technologies, Inc., Nashville, TN (US)

(*) Notice: Subject to any disclaimer, the term of this patent is extended or adjusted under 35 U.S.C. 154(b) by 0 days.

(21) Appl. No.: 09/284,955

(22) PCT Filed: Nov. 3, 1997

(86) PCT No.: PCT/US97/19690

§ 371 Date: Jul. 14, 1999

§ 102(e) Date: Jul. 14, 1999

(87) PCT Pub. No.: WO98/19800

PCT Pub. Date: May 14, 1998

Related U.S. Application Data
(60) Provisional application No. 60/030,185, filed on Nov. 4, 1996.

(51) Int. Cl.$^7$ .................................................. B07C 5/342
(52) U.S. Cl. ..................... 209/587; 209/577; 209/578; 209/579; 356/301
(58) Field of Search .................... 209/576, 577, 209/578, 579, 587; 356/301

(56) References Cited

U.S. PATENT DOCUMENTS

| | | | |
|---|---|---|---|
| 3,747,755 | * 7/1973 | Senturia et al. .................. 209/559 |
| 4,397,556 | * 8/1983 | Muller ................................ 356/301 |
| 4,575,629 | * 3/1986 | Schnell et al. .................... 250/238 |
| 4,693,377 | * 9/1987 | Gerrard et al. ................... 209/579 |
| 4,823,166 | * 4/1989 | Hartog et al. ..................... 356/44 |
| 4,856,897 | * 8/1989 | Fateley et al. .................... 356/301 |
| 5,134,291 | 7/1992 | Ruhl, Jr. et al. ................. 250/341 |
| 5,144,374 | * 9/1992 | Grego ................................. 356/326 |
| 5,206,699 | * 4/1993 | Stewart et al. .................... 356/30 |
| 5,256,880 | * 10/1993 | Loree et al. ...................... 250/461.1 |
| 5,351,117 | * 9/1994 | Stewart et al. .................... 356/30 |
| 5,361,912 | 11/1994 | Krieg et al. ...................... 209/24 |
| 5,459,313 | * 10/1995 | Schrader et al. ................. 250/223 B |
| 5,553,616 | * 9/1996 | Ham et al. ........................ 600/316 |
| 5,617,206 | * 4/1997 | Fay .................................... 356/320 |
| 5,628,410 | * 5/1997 | Smith et al. ...................... 209/579 |
| 5,786,893 | * 7/1998 | Fink et al. ........................ 356/301 |
| 5,866,430 | * 2/1999 | Grow ................................. 436/172 |
| 5,963,319 | * 10/1999 | Jarvis et al. ...................... 356/301 |
| 6,007,994 | * 12/1999 | Ward et al. ....................... 435/6 |
| 6,044,285 | * 3/2000 | Chaiken et al. .................. 600/316 |
| 6,091,491 | * 7/2000 | Chisholm et al. ................ 356/301 |

OTHER PUBLICATIONS

Kreyszig, E., Advance Engineering mathematics, *Linear Algebra, Part 1: Vectors*, 5th Ed. Chapter 6: 247–279.

Bishop, C., Neural Networks for Pattern Recognition, *Single Layer Networks*, Chapter 3–6:77–252; Chapter 9–10:332–439.

* cited by examiner

Primary Examiner—Donald P. Walsh
Assistant Examiner—Daniel K Schlak
(74) Attorney, Agent, or Firm—Foley & Lardner

(57) ABSTRACT

A high accuracy rapid system for sorting a plurality of waste products by polymer type. The invention involves the application of Raman spectroscopy and complex identification techniques to identify and sort post-consumer plastics for recycling. The invention reads information unique to the molecular structure of the materials to be sorted to identify their chemical compositions and uses rapid high volume sorting techniques to sort them into product streams at commercially viable throughput rates. The system employs a laser diode (20) for irradiating the material sample (10), a spectrograph (50) is used to determine the Raman spectrum of the material sample (10) and a microprocessor based controller (70) is employed to identify the polymer type of the material sample (10).

23 Claims, 8 Drawing Sheets

APPLICATION OF RAMAN SPECTROSCOPY TO IDENTIFICATION AND SORTING OF POST-CONSUMER PLASTICS FOR RECYCLING

CROSS-REFERENCE TO RELATED APPLICATION

This application claims the benefit of U.S. Provisional Application No. 60/030,185 filed Nov. 4, 1996.

STATEMENT REGARDING FEDERALLY SPONSORED RESEARCH AND DEVELOPMENT

The invention was made with the support of the United States Government under Contract No. DE-FG02-95ER82038 awarded by the U.S. Department of Energy. Therefore, the United States Government has certain rights in the invention.

The present invention has been the subject of the aforementioned provisional application in the United States as well as an application for a grant from the United States Department of Energy (Application No. 35343-95-I). The contents of these two documents are herein incorporated by reference, in their entireties.

BACKGROUND OF THE INVENTION

The invention relates to the identification and sorting of plastic refuse. Specifically, the invention involves the application of Raman spectroscopy to identification and sorting of post-consumer plastics for recycling.

Society has reaped much benefit from the use of plastics over the past decades. The strength, lightness and versatility of products made from plastic makes their use advantageous over many other materials. Disposal of the products made from plastics, however, has clearly been a problem. Post-consumer plastics have become a tremendous burden upon our waste disposal systems. Plastics constitute only about 9% by weight of municipal solid waste but they occupy approximately 25% of the volume of the waste stream.

Recycling is one major solution to the problem of disposal. Diversion of plastics from landfill to recycling can potentially save the energy equivalent of 60 million barrels of oil annually. In addition, new applications for and products made from recycled post-consumer plastics are being developed each day. Some of these applications and product include the production of fiber for clothing and carpeting, durable goods, consumer goods packaging, and food and beverage packaging.

However, post-consumer plastics recycling is expensive and not cost-effective when the plastics are unsorted. Mixed plastics are of little or no economic value and have limited marketability. To be cost-effective, it is necessary for mixed plastics to be sorted according to chemical composition.

Currently, there are various techniques for identifying and sorting materials by polymer type. Some of these techniques include manual hand sorting, density separation, and various automated "sense/sort" systems. Hand sorting is tedious, expensive, prone to error, and can be unsafe. Density separation of granulated plastics by sink/float in a water bath yields only a float product and a sink product and is not useful for a primary sort of mixed plastics. Sensing methods used in automated sense/sort systems include x-ray analysis, optical inspection using photodiodes or CCD machine vision, and near infrared (NIR) sensing. X-ray analysis is effective only for separating polyvinyl chloride (PVC) plastics from polyethylene terephthalate (PETE) plastics. Optical scanning of post consumer plastics is useful for sorting plastics according to transparency and color but is unable to provide chemical identification of polymers. Application of NIR technology to plastic waste sorting remains largely unproven. A new cost effective technology is needed that can accurately identify and sort plastics by polymer type at high throughput rates.

SUMMARY OF THE INVENTION

The present invention provides the cost effective technique needed in the industry and performs high speed sorting more accurately than any other technology known to the inventors.

The present invention uses Raman spectroscopic sensing and complex identification techniques to identify the polymer type of a sample and to sort accordingly. Research has determined that the Raman spectra within a given group of polymers is very different from the Raman spectra of polymers in another group. This difference is identifiable and can provide the basis of a sort. Through the present invention, the Raman spectra of polymers within a given group, which are not very different, can also be differentiated in most cases. This identification technique in combination with a reliable sorting apparatus results in the breakthrough technology of the present invention for high speed accurate identification and sorting of mixed streams of plastics.

It is a primary object of this invention to provide a high accuracy rapid system for sorting waste plastics by polymer type.

It is a further object of this invention to identify and sort a plurality of materials by polymer type largely independent of sample positioning (depth of field).

It is another object of this invention to identify and sort a plurality of materials by polymer type largely irrespective of the color of the material.

It is still another object of this invention to identify and sort a plurality of materials by polymer type largely irrespective of the existence of contaminants commonly found on the plastic to be sorted.

It is yet another object of this invention to identify and sort a plurality of materials by polymer type even when the material is presented at high speed and thus, for a low exposure time.

Another object of this invention is to identify and sort a plurality of materials by polymer type using data from a broad Raman spectrum of a material sample, instead of from solely a narrow wavelength band, in order to more accurately identify its polymer type.

Other objects, features and advantages of the present invention will become apparent to those skilled in the art from the following detailed description. It should be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

The disclosed invention further employs a sophisticated method for rapid identification and sorting of a plurality of materials by polymer type comprising the steps of:

a) conveying at least one of said plurality of materials;

b) irradiating material conveyed with light from a laser to induce Raman emission;

c) collecting the light reflected from the said material;
d) performing a spectroscopic analysis of the collected light to determine its Raman spectra;
e) identifying the polymer type of said material by comparing said Raman spectra with a database of spectra of at least one known polymer type; and
f) sorting said plurality of materials by identified polymer type.

In the present invention, the step of identifying the polymer type of the material can further comprise the use of baseline correction to reduce the effect of fluorescence and other background noise. The step of identifying the polymer type of the material can also comprise the use of a vector dot product algorithm to perform the comparison of the Raman spectra of the material with the spectra of known polymers in the database.

Also, the inventors disclose a system for rapid recognition and sorting of a plurality of materials by polymer type, said system comprising:

a feed conveyor for conveying said plurality of materials;

a laser diode for providing irradiating light of a determinable frequency;

a probe head, coupled to said laser diode, for irradiating at least a portion of at least one of said conveyed plurality of materials with said irradiating light and inducing Raman emission from the irradiated material and for collecting reflected light energy from the irradiated material;

a spectrograph, coupled to said probe head, for analyzing the collected reflected light to determine its frequency components and outputting data corresponding to said frequency components, and a microprocessor based controller, coupled to said spectrograph means, for controlling the spectrograph and for processing the said data corresponding to the frequency components of the collected reflected light to identify the irradiated material as a recognized polymer type and to generate a signal to indicate whether the irradiated material should be separated, and a sorter, coupled to and controlled by said microprocessor based controller, wherein said sorter separates said plurality of materials in accordance with said signal.

BRIEF DESCRIPTION OF THE DRAWINGS

The present invention will be described below with reference to the accompanying drawings, wherein.

DETAILED DESCRIPTION OF THE PREFERRED EMBODIMENTS

The present invention uses Raman spectroscopic sensing and complex identification techniques to provide a high accuracy rapid system for sorting waste plastics by polymer type. The present invention reads information unique to the molecular structure of the plastics to identify their chemical compositions and uses rapid high volume sorting techniques to sort them into product streams at commercially viable throughput rates.

Raman shift is caused by the transfer of energy from a photon to a molecule, with the frequency of the light reflected being dependent upon the amount of energy absorbed by the molecule. Since the energy states of a molecule are quantized, with the quantum energy states being dependent upon molecular structure, energy peaks are found which represent differences in molecular structure.

Figure 1:
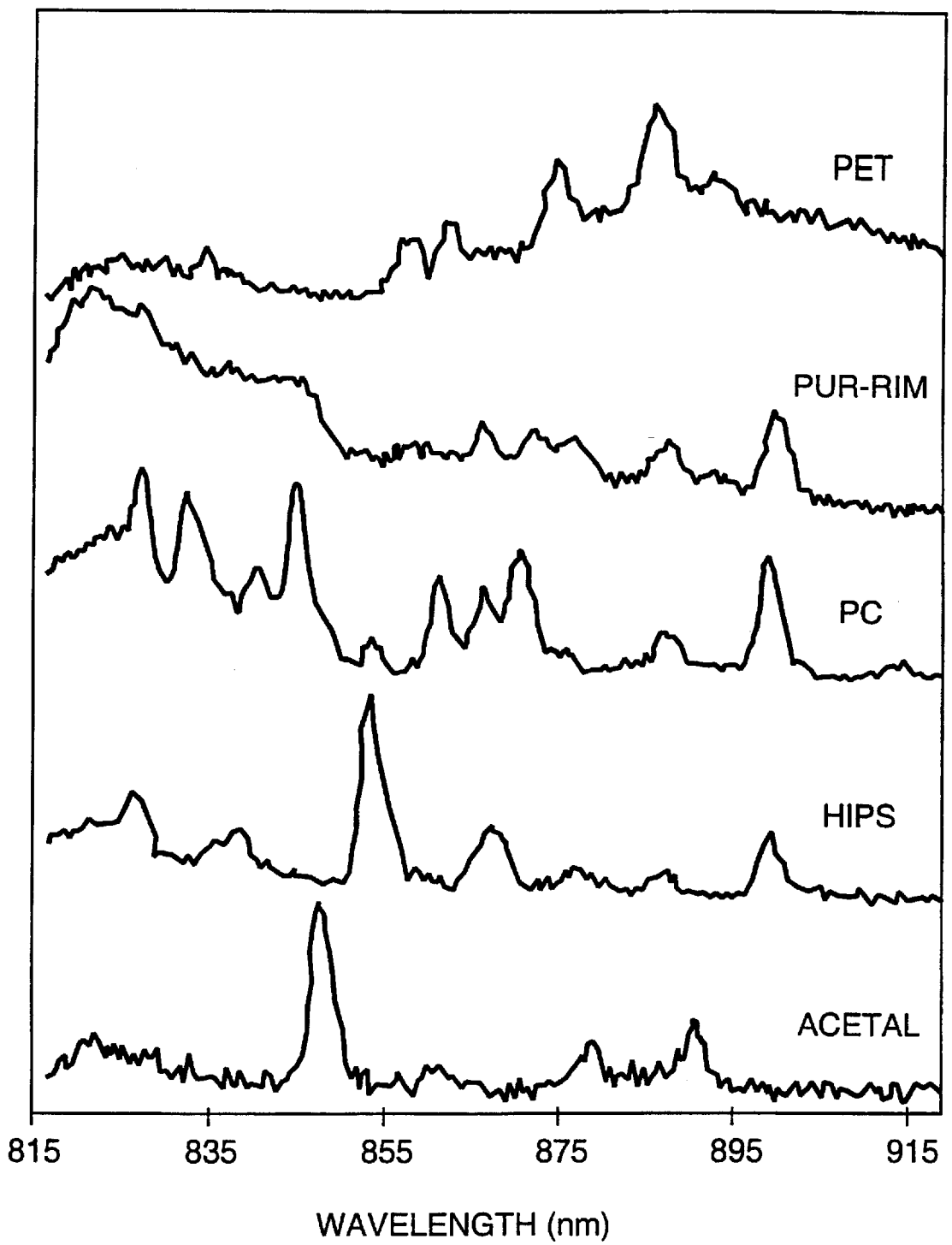
FIG. 1 shows the Raman spectra of selected post-consumer waste containers.

Raman spectra within a given group of polymers is very different from the Raman spectra of polymers in another group. This difference is identifiable and can provide the basis of a sort. The Raman spectra for some typical post-consumer plastics are shown in FIG. 1. These spectra were obtained in 2 seconds using a 785 nm 500 mW diode excitation laser.

Through the present invention, the Raman spectra of polymers within a given group, which are not very different, can also be differentiated in most cases. This identification technique in combination with a reliable sorting apparatus results in the breakthrough technology of the present invention for high speed accurate identification and sorting of mixed streams of plastics.

Figure 2:
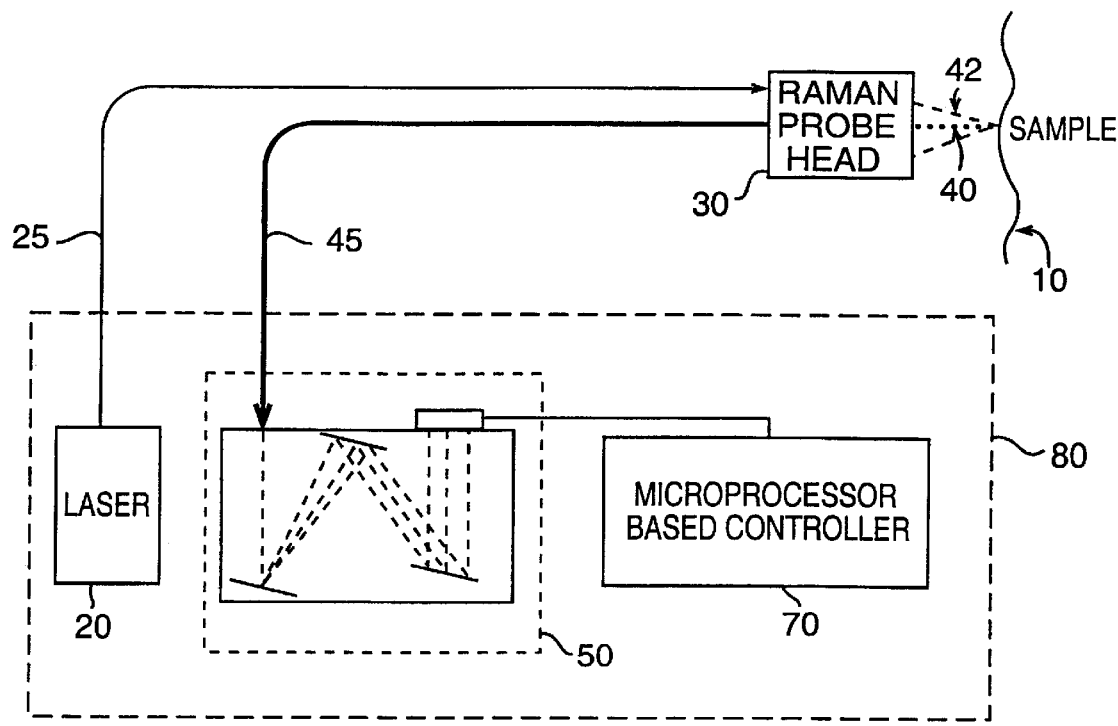
FIG. 2 shows a block diagram of a Raman identification system.
Figure 3:
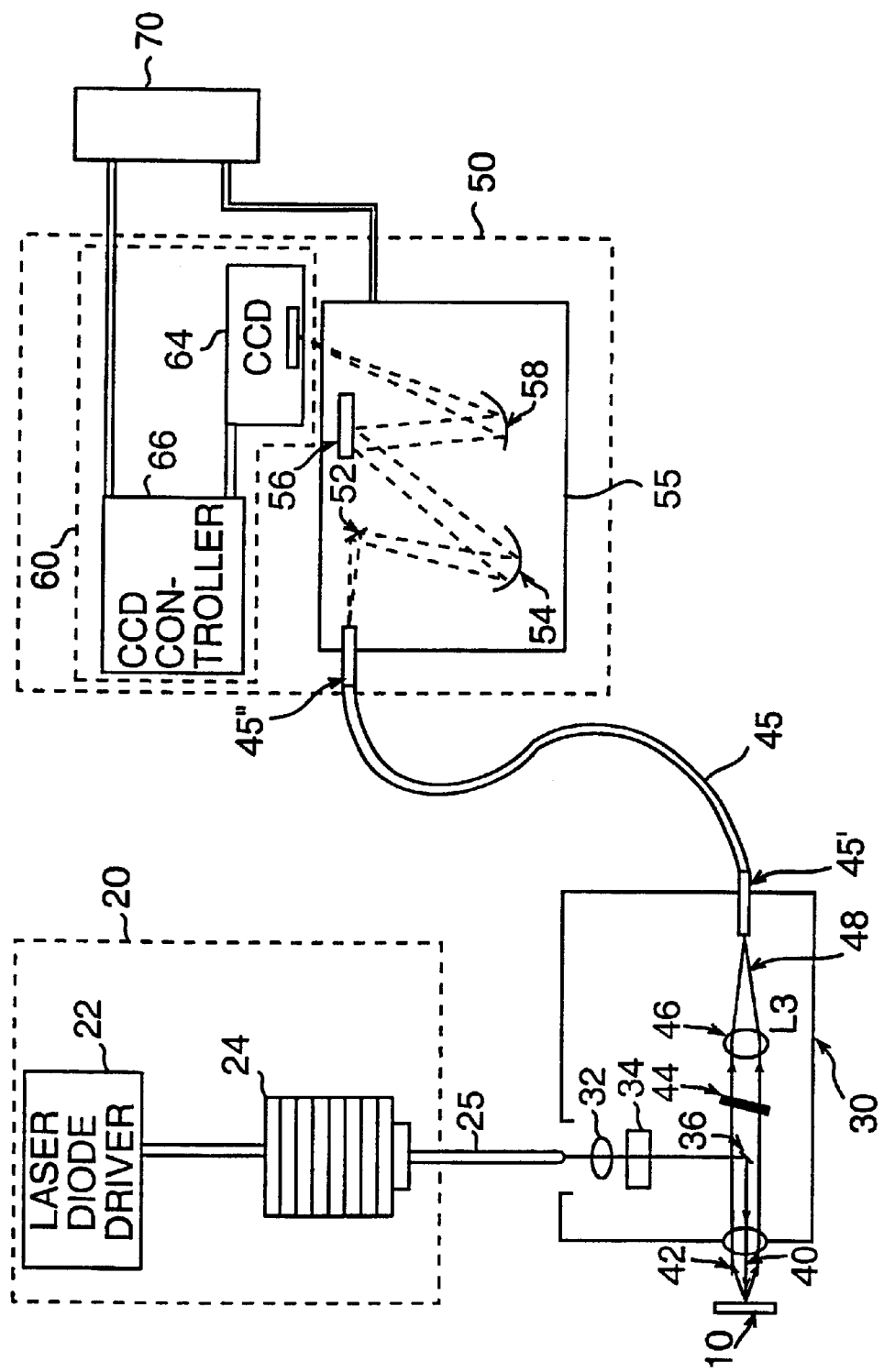
FIG. 3 shows a detailed schematic of a Raman identification system.

FIG. 2 shows a block diagram of the identification system using Raman spectroscopy of the present invention. The identification system as shown in FIG. 2 has four principal components. The first component is a laser diode 20 that generates light for irradiating a material sample 10. The second component is a probe head 30 coupled to the laser diode 20 for irradiating the material sample 10 with light 40 intended to induce a Raman emission, including both Stokes and anti-Stokes radiation. The probe head further collects the reflected light 42 including the Raman signal. The third component is a spectrograph 50 coupled to the Raman probe head 30 to determine the Raman spectrum of the material sample 10. The spectrograph 50 includes a spectroscope 55 as well as a CCD (charge-coupled device) detector 60, as shown in FIG. 3. The fourth principal component of the identification system of the present invention is the microprocessor based controller 70 which is coupled to the spectrograph. The microprocessor based controller 70 controls the spectrograph and uses techniques developed by the inventors to identify the polymer type of the material sample 10 based upon its Raman spectrum.

The method and apparatus of the present invention are now described in greater detail with reference to FIG. 3 which shows a detailed schematic of the Raman identification system of the present invention.

In the present invention, a light energy source, preferably a laser 20, is used to generate irradiating light. The irradiating light can be visible light or light outside the visible spectrum such as ultraviolet or infrared. It is preferred that the irradiating light be substantially monochromatic. One method for ensuring the irradiated light is substantially monochromatic is to use a laser as the light energy source, such as laser 20, so that the wavelength of the generated light is highly determinable. In the preferred embodiment, a laser with a center wavelength of 785 nm (+/−4 nm) is used. One such laser consists of components from Spectra Diode Labs (SDL) Inc. including an SDL-800 1.0 amp diode drive with TE cooling controller, an SDL-800-H heat sink assembly and an SDL 2352-H1 laser diode.

Another method for ensuring the irradiating light is substantially monochromatic is to use a narrow band pass filter. This method is also used in the present invention and will be discussed. The laser 20 comprises a laser diode driver 22 and laser diode 24. The irradiating light generated by the laser 20 is provided to the probe head 30 via a coupling 25. This coupling 25 is preferably comprised of optical fibers.

As shown in FIG. 3, irradiating light enters the probe head 30 and passes through lens 32. This lens 32 serves to collimate the irradiating light generated by the laser. This collimated light is then passed through a laser band pass filter 34 which serves to ensure the irradiating light is substantially monochromatic. This band pass filter 34 strips off any laser side band emissions in the irradiating light and, in the preferred embodiment, limits the bandwidth to within +/−2 nm of the center wavelength of the laser 20, 785 nm. After passing through the band pass filter 34, the irradiating light is redirected by a small mirror 36 into a lens 38 which focuses the irradiating light 40 onto the sample 10. This induces a Raman emission. Lens 38 also serves to collect the light reflected 42 from the sample 10, including the Raman scattered emission.

Since the Raman scatter occurs from the surface of the sample 10 in all directions, the amount of signal collected depends, to a large extent, upon lens 38. The choice of lens 38 and the distance of the sample 10 from the focal point of lens 38 can, therefore, impact the sensitivity of the identification system. For a commercial application, it would be desired that a precise sample positioning not be required. The present invention allows for operability even when the material sample to be identified is not precisely at the focal point of a collection lens, such as lens 38. The focal length most often used in the testing of the present invention for the lens 38 was 35 mm. Focal lengths of 60 mm, 100 mm and 150 mm of lens 38, were also used with satisfactory results. Through testing, it was determined that the system becomes less sensitive to sample positioning with respect to focal point of a collection lens as the focal length increased. The drawback is that, in general, the strength of the collected Raman signal decreases as the focal length of the collection lens increases. Through years of experience in sorting technologies, the inventors have determined that sample position within a 12 mm range is achievable. Through testing, it was found that by using a collection lens with a focal length of 150 mm, the system was substantially insensitive to sample positioning over a 12 mm range. The use of higher sensitivity equipment compensates for the diminished signal strength.

Referring again to FIG. 3, the light reflected 42 from the irradiated material sample 10 is collected and collimated by lens 38. The light then passes past the mirror 36 to a holographic notch filter 44. This filter 44 blocks substantially all of light reflected from the sample having the same wavelength as the irradiating light, 785 nm in the preferred embodiment, while allowing substantially all of the remainder of the light, comprised mostly of the Raman emission, to pass through. After passing through the holographic notch filter, the remaining light 48 is focused onto a fiber coupling 45',45 through lens 46.

The foregoing describes the elements within a typical probe head, and specifically, the probe head utilized in much of the testing of the present invention, the SpectraCode RS-2. It should be understood that other probe heads with differing designs can be used in the present invention to achieve the same results. It should also be made clear that by using information from a broad Raman spectrum of a material sample, instead of from solely a narrow wavelength band, enables the present invention to more accurately identify the polymer type of the material sample.

The light 48 is presented at the spectrograph 50 via the coupling 45. In the preferred embodiment, the fiber coupling 45 consists of nineteen 200 $\mu$m fibers. At the probe head end 45', these fibers are bundled in a circular design for optimum light collection. At the spectrograph end 45" of the coupling 45, these fibers are arranged in a linear stack to simulate a slit allowing for a more efficient transmission of light to the spectrograph 50. Within the spectrograph 50 is a spectroscope 55 which separates light into it spectral components. The light from the coupling 45 enters through a slit of the spectroscope 55. A plane mirror 52 reflects the light onto mirror 54. This mirror 54 collimates the light and reflects it onto the grating 56. In the spectroscope 55 used in testing the present invention, the grating 56 is on a turnstile (not shown) which holds two separate gratings and allows for remote control of the grating angle which governs the central wavelength. In the preferred embodiment, 860 nm is used as the central wavelength of the grating. This wavelength is adjustable; for the identification of some polymer types, it is more effective to use a different central wavelength. Light scattered from the grating is reflected by mirror 58 and focused onto the exit plane 62 of the spectroscope. The spectroscope 55 is controlled via the microprocessor based controller 70. As with the probe head, the foregoing only serves to describe the elements within a typical spectroscope and specifically, the spectroscope utilized in much of the testing of the present invention, Acton Research Corporation's SpectraPro-150. It should be understood that other spectroscopes with differing designs can be used in the present invention to achieve the same results.

Also within the spectrograph 50 is the CCD (charged-coupled device) detector 60 which further comprises a CCD controller 66 and a CCD camera 64. The CCD detector serves to accept as input the spectral information provided at the exit plane 62 of the spectroscope and provides as output a data signal corresponding to the frequency components of the light 48. The CCD camera is mounted at the exit plane 62 of the spectroscope 55. The CCD detector is coupled to the microprocessor based controller 70 enabling the CCD detector to be controlled by the microprocessor controller 70 via the CCD controller 66 and also for enabling the microprocessor based controller 70 to receive the output data signal of the spectrograph 50 corresponding to the frequency components of the light 48. In much of the testing of the present invention, the CCD detector used was Santa Barbara Instrument Group's ST-6I TE cooled CCD camera. The coding of the control software and the drivers is dependent upon the design selection made for the CCD detector 60 and the spectroscope 55.

Figure 6A:
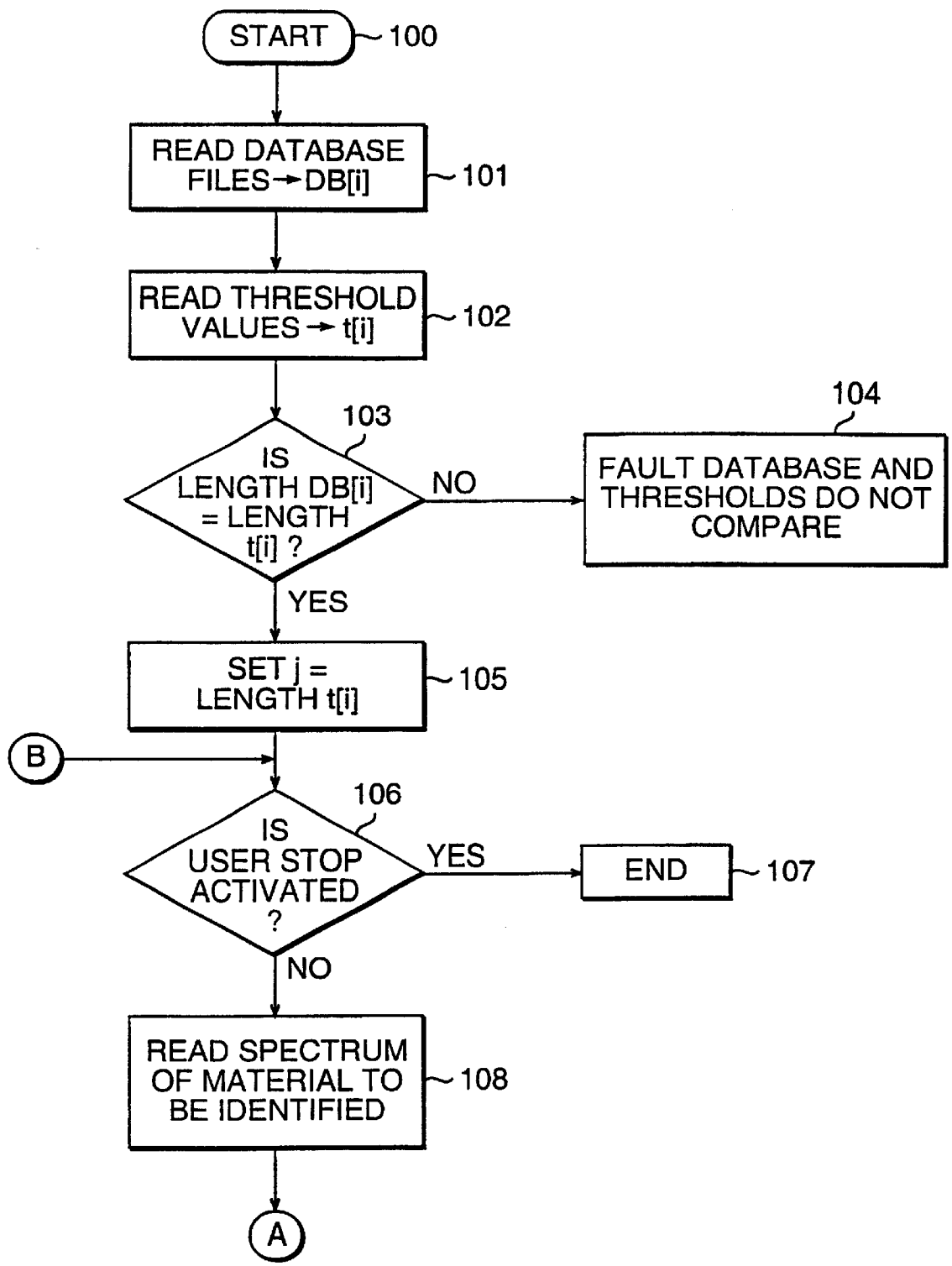
FIGS. 6A–6C show the steps performed in identifying the polymer type of a material sample from its Raman spectrum.
Figure 6B:
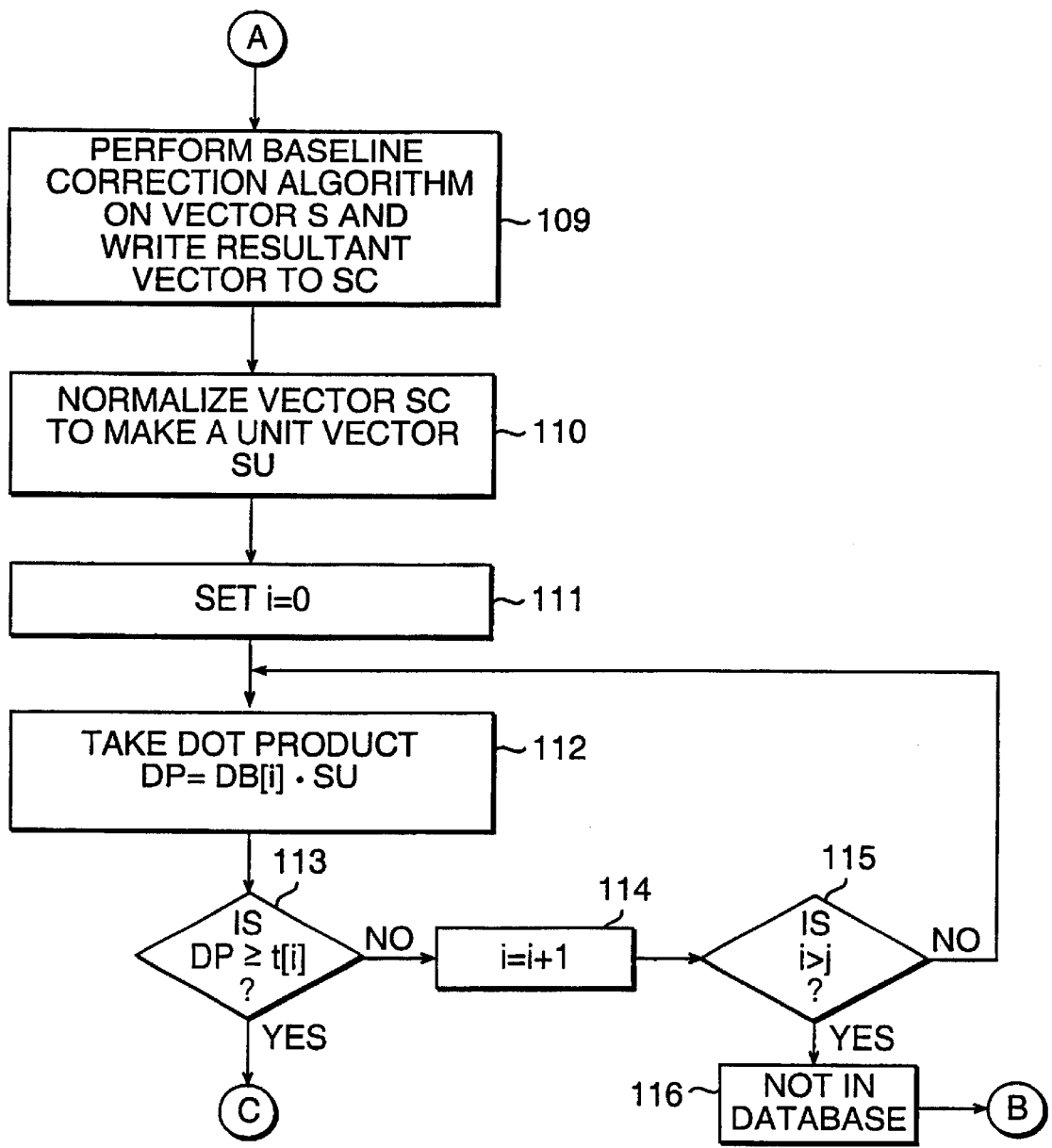
Figure 6C:
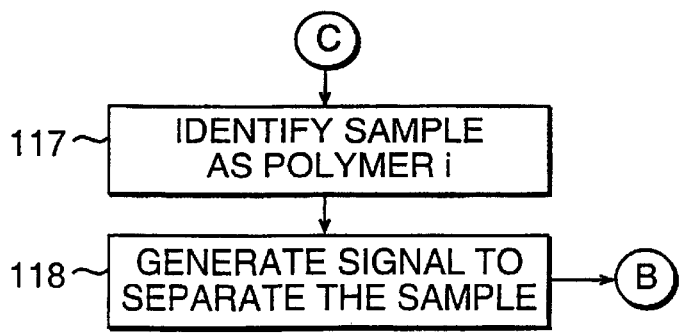

The microprocessor based controller 70 performs much of the analysis to identify the polymer type of the material sample 10. The microprocessor based controller 70 comprises at least a microprocessor and a memory. One of the functions of the memory is for the retrieval of Raman spectrum data corresponding to at least one known polymer type. The Raman spectra of various known polymer types can be obtained and formatted in a way discussed herein for storage in database files. The microprocessor based controller used for much of the testing of the present invention was a Pentium™ based PC. The material identification technique used by the microprocessor based controller 70 is shown in FIGS. 6A–6C, the baseline correction technique of which is further shown in FIGS. 7A and 7B. Both techniques will be discussed in detail in connection with the descriptions of FIGS. 6A–6C, 7A and 7B. Using these techniques, the contents of the database files and the data received from the spectrograph, a determination can be made, through the microprocessor based controller 70, as to whether the material sample 10 is of a recognized polymer type and, if so, what particular polymer type it is. This determination has great utility in accurately sorting a plurality of materials. The application of the system for identifying materials by polymer type to the function of sorting is described below.

Figure 4:
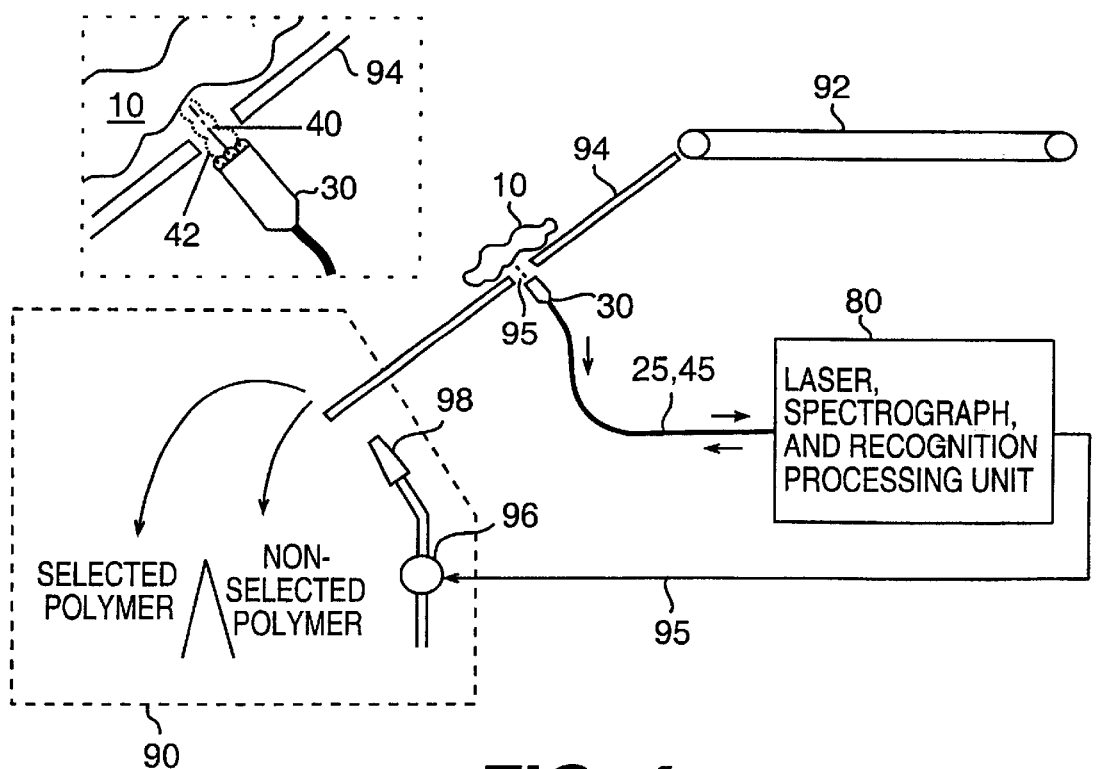
FIG. 4 shows a prototype sorting system using Raman spectroscopy.

FIG. 4 shows a prototype sorting system using Raman spectroscopy. In a high speed sorting system, it is necessary to acquire spectra from the material samples as they move through a sensing region. FIG. 4 shows an infeed conveyor 92 by which each of the material samples 10 is conveyed. It should be noted that the infeed conveyor may be a belt conveyor, a slide, a vibrating pan conveyor, a free fall trajectory, or any other means for conveying materials. In the configuration shown in FIG. 4, the material sample 10 is then placed upon a ramp 94 wherein the combination of initial velocity and the force of gravity causes it to slide down the ramp 94. The rate at which the material sample 10 slides can be affected by the declination angle of the ramp 94. A typical angle is 45° from the horizontal. The material sample 10 passes over an opening 95 in the ramp 94 wherein it is exposed to irradiating light 40 through the probe head 30. The probe head also collects the reflected light 42. The probe head is coupled to the laser (not shown) and the spectroscope (not shown) within the sensing system 80 through couplings 25 and 45 shown as a bundled coupling 25,45. The material sample 10 is analyzed as described above and identified. A control signal is then sent from the microprocessor based controller (not shown) within the sensing system 80 to a sorting means 90 and specifically to an air solenoid 96 through a coupling 95. The air solenoid 96 is connected to and controls the flow of air from an air reservoir (not shown) to an air nozzle 98. Upon identification of the material sample 10 as being of a recognized and selected polymer-type, an appropriately timed control signal is sent from the sensing system 80 to the air solenoid 96 to allow air to flow to the air nozzle 98 thus redirecting the material sample 10 into a specific area designated for selected polymers. This procedure repeats as each of the plurality of material samples is conveyed by the infeed conveyor 92 until all of the samples have been analyzed and a complete sort has been performed. While FIG. 4 shows a sorting means in which materials are separated into two areas, it should be clear that the sorting means can be configured to separate materials into more than two areas as well.

Figure 5:
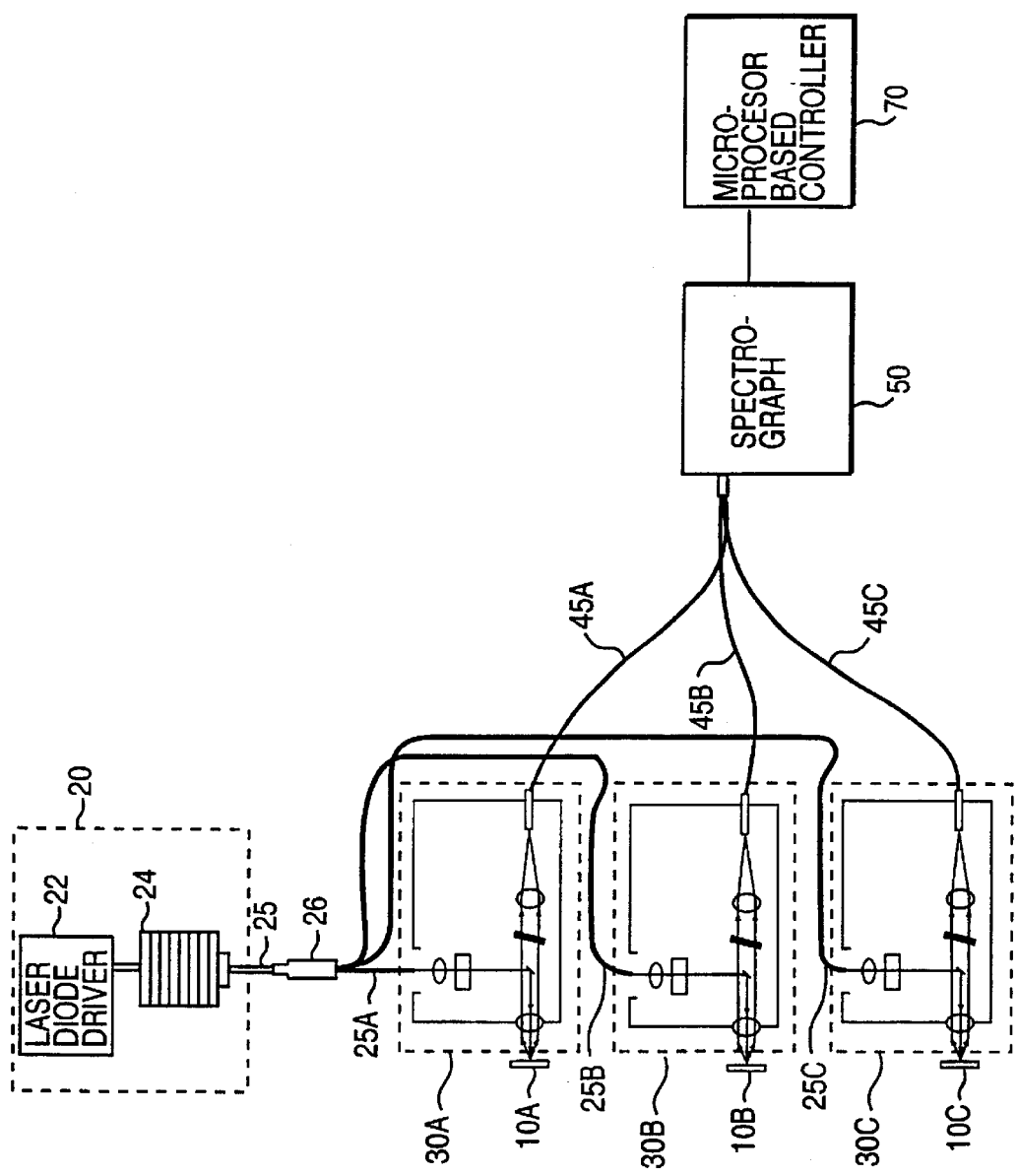
FIG. 5 shows a multiple probe head configuration for a Raman identification system.

FIG. 5 shows an embodiment with a multiple probe head configuration for a Raman identification system of the present invention. It should be apparent that this method and configuration may also be applied to the sorting function as described above in connection with FIG. 4. In this embodiment in which a single laser 20 and a single spectrograph 50 can be utilized to perform simultaneous multiple channel identification and sorting. This provides a more cost-effective way for a plurality of materials in different locations to be identified and sorted in parallel over the use of three lasers and certainly over the use of multiple spectrographs.

The method used in the system shown in FIG. 5 is similar to that described in connection with FIG. 3. In this embodiment, however, the irradiating light from the laser 20 is split by low-loss beam splitter 26, or by splitting fiber 25 into three fibers, and coupled to probe heads 30A, 30B and 30C through coupling 25A, 25B and 25C respectively. Each of the material samples 10A, 10B and 10C are irradiated and the reflected light is collected as described in connection with FIG. 3. The multiple probe heads are coupled to the spectrograph 50 through couplings 45A, 45B and 45C respectively. The spectrograph 50 is of the type capable of analyzing a plurality of light signals, such as the combination of an Instruments S.A. TR180-MS3 spectroscope and an Instruments S.A. MSL-TSH CCD. The microprocessor based controller 70 performs in the manner described in connection with FIG. 3.

While FIG. 5 shows, for purposes of example, the use of three probe heads to irradiate three material samples. It should be apparent that any number of probe heads can be used to irradiate any number of material samples. Known limitations on the maximum number of material samples that could be analyzed in parallel with a single laser and single spectrograph are the power of the laser and the capability of the spectrograph to analyze large numbers of spectra. Alternatively, each probe head 30A, 30B and 30C could be fed by separate lasers.

As mentioned, the microprocessor based controller 70 performs much of the analysis to identify the polymer type of the material sample 10 in the systems described above. The material identification algorithm used by the microprocessor based controller 70 is shown in FIGS. 6A–6C, the baseline correction function of which is further shown in FIGS. 7A and 7B.

Beginning with FIG. 6A, step 100 indicates the start of the identification algorithm. In step 101, the contents of the database files are read into memory. For ease of description, the memory locations into which the database files are read are shown as DB[i]. These database files contain previously acquired data corresponding to the Raman spectrum for various polymer types. It is possible that the database may contain only a subset of the known polymer types if the scope of the identification can be so limited. The database files are read into memory to improve system performance by reducing the amount of time spent accessing data from the files. This step 101 is performed before the data from the first material sample is analyzed. In step 102, the threshold values are read into memory at t[i]. These threshold values, one value for each of the polymer types, set the maximum deviation from a perfect match for which the material sample will still be identified as being made of the polymer type to which it is being compared. The use of the threshold values will be further explained in connection with step 113.

In step 103, a check is made to ensure that the number of database files read into memory, shown as Length DB[i] is equal to the number of threshold values read into memory, shown as Length t[i]. If not, a fault condition is expressed to the user in step 104. Assuming no fault has occurred, step 105 will be performed and a variable j will be set to length of t[i], which is equivalent to the number of different polymer data files read into memory from the database in step 101. In step 106, a check is made to determine whether a user stop has been activated, that is, whether the user has initiated a termination of the program. If there is an indication of user stop activation, then the program ends in step 107. Otherwise, in step 108, the spectrum of the material sample 10 to be identified is obtained and read from the output of the spectrograph 50 into a memory array referred to as vector S, where vector S is constructed of coordinate points defined as magnitude of an energy value associated with a directional component corresponding to wavelength along the Raman spectrum.

Figure 7A:
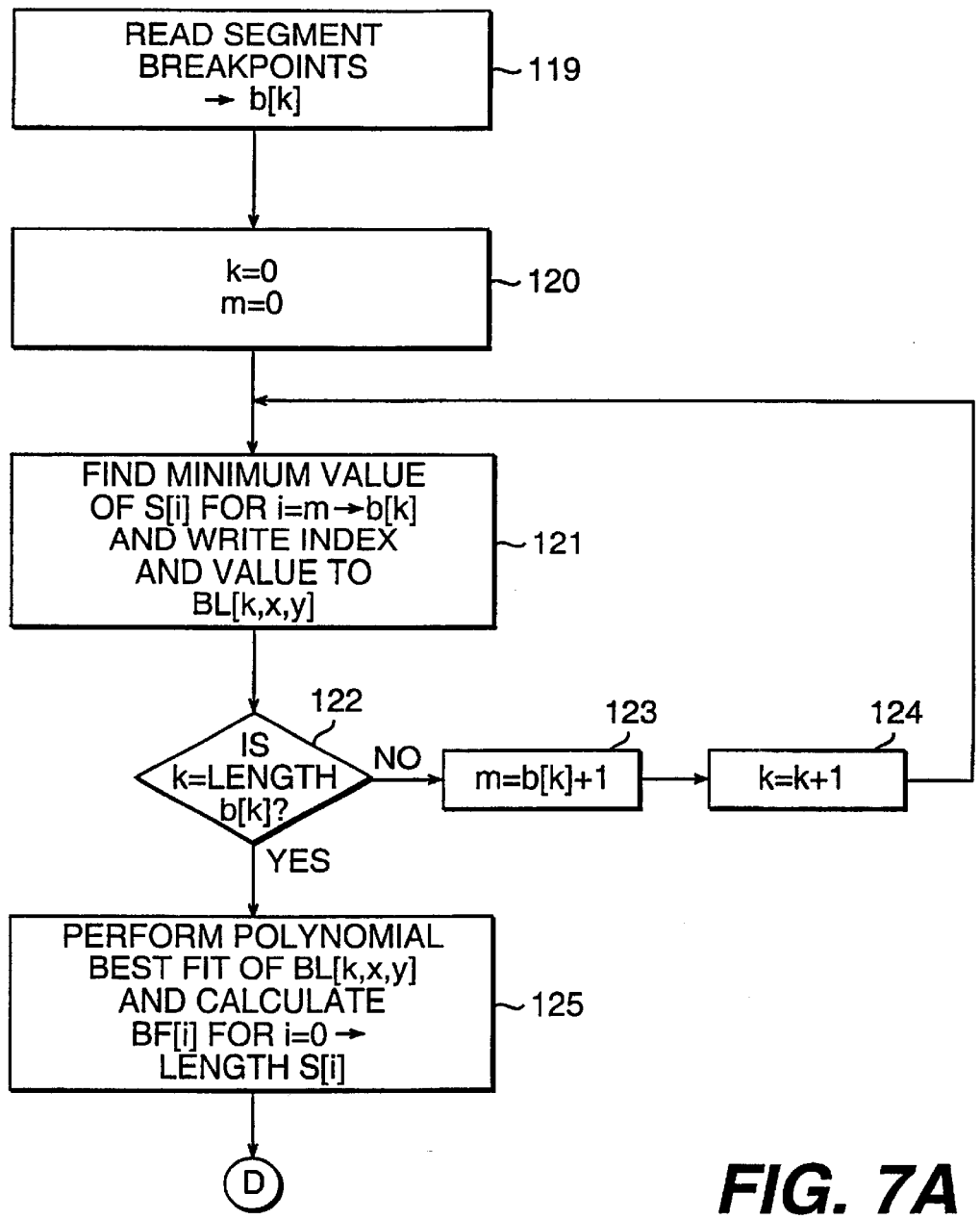
FIGS. 7A and 7B show the steps performed in correcting the baseline of Raman spectrum data.
Figure 7B:
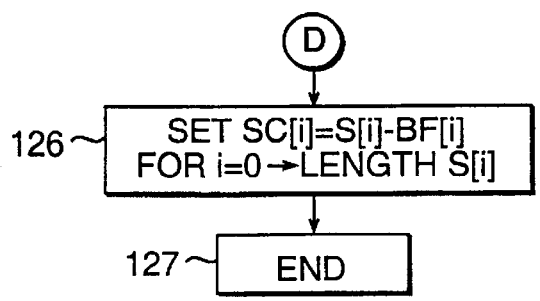

The program continues in FIG. 6B, step 109 wherein a baseline correction is performed on the data in vector S and the resulting baseline corrected data is stored in vector SC. This baseline correction is shown in FIGS. 7A and 7B and is performed to reduce the effects of fluorescence and other background noise that would otherwise erroneously increase the intensity of the Raman spectrum of the material sample. Performing this baseline correction significantly enhances the quality of the Raman spectrum and the accuracy of the identification system. In step 119 of FIG. 7A, the segment breakpoints are read into memory in b[k]. The set of data corresponding to the Raman spectrum of a material sample consists of the same number of data points as is stored in the database files for each of the various polymer types. Segment breakpoints are the points at which the entire set of data corresponding to the Raman spectrum of the material sample is separated for the purposes of finding minimum values. For example, if the entire set of data for a material sample stored in vector S consisted of 300 data points, a possible set of segment breakpoints would consist of the values 100 and 200 in order to separate, solely for the purposes of baseline correction, the set of 300 points into smaller sets of approximately 100 points. In step 120, counters k and m are set to zero. In step 121, the minimum value for a subset of vector S is found, from the first data point to the data point of the first breakpoint, and is written to BL[k,x,y] where k=the value of k, x=the actual data point number and y=the value of that data point (intensity). For example, if the first breakpoint, b[0], is 100, then the minimum value S from S[0] to S[100] is found. If this minimum value is 37,500 which occurs at S[64], then the data written would be to BL[0,64,37500]. In step 122 the value of k is compared to the length of b[k], that is the number of breakpoints. If k has not yet reached the total number of breakpoints, then steps 123 and 124 are performed before returning to step 121. In step 123, the value of m is set to the breakpoint plus 1 and in step 124 the value of k is incremented by one. Step 121 is now repeated with the new values of m and k to find the minimum value within the next subset of vector S. This loop is repeated until a minimum value has been found for each subset of vector S. Then, in step 125, a polynomial best fit is calculated for the x,y data pairs stored in BL[k,x,y], the number of data points being equivalent to the length of b[k]. Upon calculation of the polynomial best fit, a best fit baseline, BF[i], is calculated for each data point. The last step in the baseline correction algorithm is shown in FIG. 7B at step 126, wherein the Raman spectrum stored in vector S is reduced by the calculated baseline in BF for each data point and the baseline corrected data in stored in vector SC.

The program, as shown in FIG. 6B, then moves on to step 110, wherein the baseline corrected data stored in vector SC is normalized to make a unit vector SU. In step 111, a counter i is set to zero. In step 112, the unit vector SU corresponding to the baseline corrected and normalized Raman spectrum of the material sample is compared to data corresponding to the Raman spectrum of a polymer from a database file already having been baseline corrected and normalized. This comparison, in the preferred embodiment, is performed by calculating a dot product DP where DP is the dot product of the vector DB and the vector SU. Background information regarding the use of dot products to compare multiple sets of data can be found in "Advanced Engineering Mathematics," Erwin Kreyszig, John Wiley & Sons, New York, 1983. In step 113, it is determined, using the value obtained for DP, whether a match has been found between the material sample and the polymer type to which it has been compared. A DP equal to 1 would indicate an exact match between the two. Since vectors DB and SU have each been normalized to be unit vectors, the value of the dot product DP cannot exceed the value of 1. However, values for DP of from zero to one are possible, with DP=0 indicating no matching energy peaks between DB and SU and DP=1 indicating an exact match of energy peaks between DB and SU. Such an exact match is somewhat unlikely and therefore, in step 113, the DP is compared to the threshold value for the particular polymer type to which the material sample is being compared. For example, the threshold value for a particular polymer type X could be 0.92. In such a case, whether a match was made with that polymer type would depend upon whether the value of DP was 0.92 or higher. If so, the material sample would be identified as being of polymer type X in FIG. 6C, step 117 and for the benefit of a sorting means, a signal would be generated in step 118 to separate the sample as being of the desired or indicated type.

If in FIG. 6B, step 113, it is determined that there is no match with that particular polymer type because the value of DP is below the threshold value, then step 114 is performed wherein the value of i is incremented to allow the system to consider the next polymer type. In step 115, it is ensured that the value of i does not exceed the total number of different polymer data files read into memory from the database in step 101. If i has a value exceeding that of j, step 116 indicates that all of the polymers originally in the database have been considered and no match was made. The program then returns to step 106 and if no user stop has been activated, in step 108 it reads the spectrum of the next material sample to be identified. Notice that steps 101–105 need not be performed more than once. Once the database files have been read into memory, they remain in memory and can be used for identification of subsequent material samples.

In addition to the vector dot product technique described above, identification of the material sample can be accomplished by computerized neural networks. Neural network techniques for identifying materials and learning patterns are described in, for example, the published text entitled "Neural Networks for Pattern Recognition," Christopher M. Bishop, Oxford University Press,. New York (1995), (hereafter "Bishop"), the disclosure of which is incorporated herein, in its entirety. Bishop chapters 3–6 describe neural network techniques as well as different error functions that can be used for training neural networks. Bishop, chapters 9 and 10 describe techniques for learning and generalization in a neural network.

Figure 8:
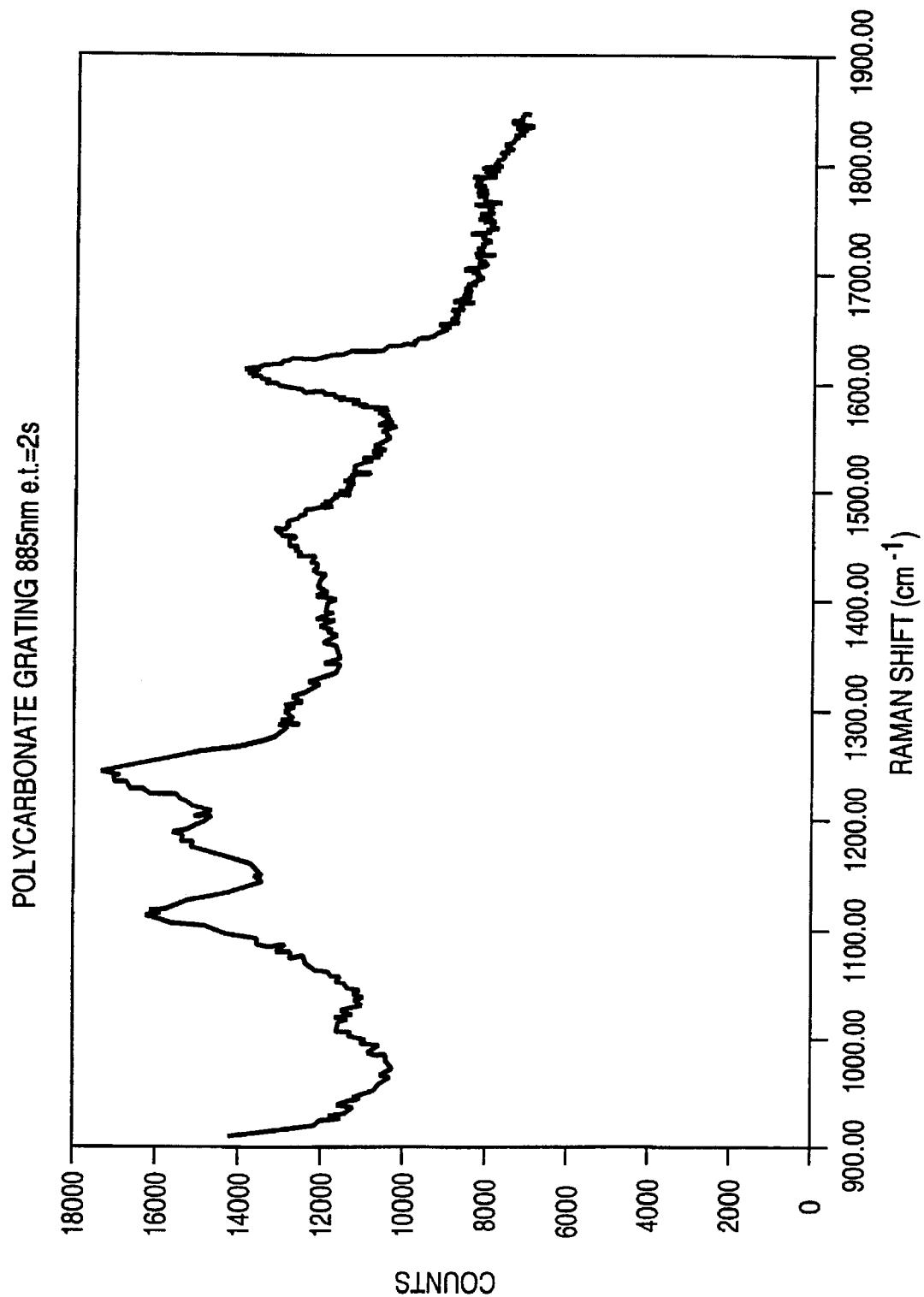
FIG. 8 shows the graphical representation of data corresponding to the Raman spectrum of polycarbonate, a polymer type commonly used in consumer goods.

FIG. 8 shows the graphical representation of data corresponding to the Raman spectrum of polycarbonate, a polymer type commonly used in consumer goods. The data underlying the graph shown in FIG. 8 was acquired by using spectroscopy in a manner which would be clear to those of ordinary skill in the art. In the same manner, based on the disclosure provided herein, data can be obtained for virtually all polymer types; polycarbonate is but one example. The graph shows the Raman shift of the measured light from the light of the irradiating source and the corresponding intensity of the measured light.

Next it is described how to place the data acquired for a particular polymer type into the format such that it can be used in the present invention. Upon acquiring the data corresponding to the Raman spectrum of a particular polymer, such as that shown graphically in FIG. 8 for polycarbonate, one first performs a baseline correction using the technique described above in FIGS. 7A and 7B, step 119 to step 126 wherein the data for the particular polymer type is substituted for the vector S. Next, one would normalize the baseline corrected data to a unit vector. The data would now be in a format to be used in the invention and would be stored to the database with an indication of the type of polymer it represents.

The velocity of the material sample through the zone in which it is irradiated and its relation to accuracy in identification was the subject of much testing. Spectra were obtained for material sample velocities of 1.25 ft/s and 3.3 ft/s. Both spectra provided adequate information for accurate identification of the material sample. Therefore, to a large extent, movement of the material sample appears to have very little effect on the performance of the present invention.

The exposure time required for accurately identifying a material sample 10 while still maintaining a rapid sorting speed was also the subject of much testing. Of course, the longer the exposure time, that is the longer a material sample is exposed to irradiating light and reflected light is collected, the greater the intensity of the collected Raman signal and the better the results of the identification system. On the other hand, rapid mass sorting requires the use short exposure times. Through testing, spectra sufficient for identification were able to be collected within 30 ms. This exposure time is satisfactory for mass sorting applications. In using the method of the present invention, the exposure time can be reduced as advances in technology provide equipment such as spectroscopes and CCD detectors of greater sensitivity and lasers of greater power. Thus, the present invention can identify and sort a plurality of materials using a low exposure time.

Experiments were performed to test the ability of the present invention to sort plastics coated with contaminants commonly encountered in recycling applications. Multiple plastic material samples of varying polymer types were coated with oil, grease, soft drink and dirt. The identification system of the present invention was able to accurately identify the polymer type of almost all of the material samples. Only those samples coated with a layer of dirt sufficiently thick such that the irradiating light could not penetrate to the material sample were not accurately identified. Thus, the present invention can identify and sort a plurality of materials by polymer type largely irrespectively of the existence of commonly found contaminants on the materials.

Because recyclable plastics come in a variety of colors, the present invention was also tested for its ability to identify and sort irrespective of color. Material samples of a single polymer type but of varying colors were analyzed. The measured Raman spectra had similar peaks indicating that the Raman sensing technology of the present invention can be used irrespectively of the color of the materials to be identified and sorted.

It should be noted that while many of the post-consumer plastics for recycling are in the form of containers, the methods and devices disclosed herein are not limited to the identification and sorting of plastic containers. The present invention has greater applicability to the identification and sorting of all types of post-consumer plastics, including containers, durable goods, automobile parts, carpets and plastic flake.

What is claimed is:

1. A method for rapid sorting of a plurality of materials by polymer type, comprising the steps of:
    a) conveying at least one of said plurality of materials;
    b) irradiating material conveyed with infrared light from a laser to induce distinguishable Raman emission;
    c) collecting the light reflected from the said material;
    d) performing a spectroscopic analysis of the collected light to determine its Raman spectra;
    e) identifying the polymer type of said material by comparing said Raman spectra with a database of spectra of at least one known polymer type; and
    f) sorting at least one of said plurality of materials by identified polymer type.

2. A method according to claim 1, wherein step (e) further comprises the step of performing a baseline correction of the Raman spectra to reduce the effect of background noise.

3. A method according to claim 2, wherein step (e) further comprises the use of a vector dot product technique to perform the comparison with the said database of spectra.

4. A method according to claim 2, wherein step (e) further comprises the use of an artificial neural network technique to perform the comparison with the said database of spectra.

5. A method according to claim 1 wherein step (c) further comprises the use of a notch-filter to block substantially all of the collected reflected light having the same wavelength as the irradiating light while allowing substantially all of the remainder of the collected reflected light, including said Raman emission, to pass through.

6. A method according to claim 1 wherein step (a) further comprises conveying said plurality of materials in a serial manner.

7. A system for rapid recognition and sorting of a plurality of materials by polymer type, said system comprising:
    a feed conveyor for conveying at least one of said plurality of materials;
    a laser for providing irradiating infrared light to induce distinguishable Raman emission;
    a probe head, coupled to said laser diode, for irradiating at least a portion of at least one of said conveyed plurality of materials conveyed by the feed conveyor with said irradiating light and inducing said Raman emission from the irradiated material and for collecting reflected light energy from the irradiated material;
    a spectrograph, coupled to said probe head, for analyzing the collected reflected light to determine frequency components and outputting data corresponding to said frequency components;
    a microprocessor based controller, coupled to said spectrograph, for controlling the spectrograph and for processing the said data corresponding to the frequency components of the collected reflected light to identify the irradiated material as a recognized polymer type and to generate a signal to indicate whether the irradiated material should be separated; and
    a sorter, coupled to and controlled by said microprocessor based controller, wherein said sorter separates at least one of said plurality of materials in accordance with said signal.

8. A system according to claim 7 wherein the feed conveyor performs said function in a serial manner.

9. A system according to claim 7, wherein the signal to indicate whether the material should be separated, also indicates the polymer type of the material and wherein said sorter separates at least one of plurality of materials in accordance with said signal.

10. A system according to claim 7, wherein said probe head further comprises a notch-filter for blocking substantially all of the collected reflected light having the same wavelength as the irradiating light while allowing substantially all of the remainder of the collected reflected light, including said Raman emission, to pass through.

11. A system according to claim 7, wherein the spectrograph further comprises:

a spectroscope for separating the frequency components of the collected reflected light; and a charged-coupled device for receiving said frequency components of the collected reflected light and outputting data corresponding to said frequency components of the collected reflected light to the microprocessor based controller.

12. A system according to claim 11, wherein the microprocessor based controller further comprises:

a database of spectral data for at least one known polymer type wherein the irradiated material is identified by the microprocessor based controller upon a comparison of the data corresponding to the frequency components of its collected reflected light with said database of spectral data for at least one known polymer type.

13. A system according to claim 12 wherein the data corresponding to the frequency components of the collected reflected light used in the microprocessor based controller includes Stokes radiation characteristics for the said Raman emission and said Stokes radiation characteristics are used in identifying the irradiated material.

14. A system according to claim 12 wherein the data corresponding to the frequency components of the collected reflected light used in the microprocessor based controller includes anti-Stokes radiation characteristics for the said Raman emission and said anti-Stokes radiation characteristics are used in identifying the irradiated material.

15. A system for rapid recognition and sorting of a plurality of materials by polymer type, said system comprising:

conveyor means for conveying at least one of said plurality of materials;

light energy source means for providing irradiating infrared light energy to induce distinguishable Raman emission;

probe means, coupled to said light energy source means, for irradiating at least a portion of at least one of said conveyed plurality of materials with said irradiating light energy and inducing said Raman emission from the irradiated material and for collecting reflected light energy from the irradiated material;

spectrograph means, coupled to said probe means, for analyzing the collected reflected light energy to determine frequency components and outputting data corresponding to said frequency components;

recognition processor means, coupled to said spectrograph means, for processing the said data corresponding to the frequency components of the collected reflected light energy to identify the irradiated material as a recognized polymer type and to generate a signal to indicate whether the irradiated material should be separated; and sorting means, coupled to said recognition processor means, for separating at least one of said plurality of materials in accordance with said signal.

16. A system according to claim 15 wherein the conveyor means performs said function in a serial manner.

17. A system according to claim 15, wherein the signal to indicate whether the material should be separated also indicates the polymer type of the material and wherein said sorting means separates at least one of said plurality of materials in accordance with said signal.

18. A system according to claim 15, wherein said probe means further comprises a notch-filtering means for blocking substantially all of the collected reflected light energy having the same wavelength as the irradiating light energy while allowing substantially all of the remainder of the collected reflected light energy, including said Raman emission, to pass through.

19. A system according to claim 15 wherein the spectrograph means further comprises:

a spectroscope means for separating the frequency components of the collected reflected light energy; and a charged-coupled device means for receiving said frequency components of the collected reflected light energy and outputting data corresponding to said frequency components of the collected reflected light energy to the recognition processor means.

20. A system according to claim 19, the recognition processor means comprising:

a microprocessor; and a database of spectral data for at least one known polymer type wherein the irradiated material is identified by the microprocessor based upon a comparison of the data corresponding to the frequency components of its collected reflected light energy with said database of spectral data for at least one known polymer type.

21. A system according to claim 20 wherein the data corresponding to the frequency components of the collected reflected light energy used in the microprocessor includes Stokes radiation characteristics for the said Raman emission and said Stokes radiation characteristics are used in the identifying the material sample.

22. A system according to claim 20 wherein the data corresponding to the frequency components of the collected reflected light energy used in the microprocessor includes anti-Stokes radiation characteristics for the said Raman emission and said anti-Stokes radiation characteristics are used in identifying the material sample.

23. A system for rapid recognition and sorting of a plurality of materials by polymer type, said system comprising:

conveyor means for conveying at least one of said plurality of materials;

light energy source means for providing irradiating infrared light energy to induce distinguishable Raman emission;

probing means comprising a plurality of probe heads, each of said plurality of probe heads coupled to said light energy source means, for irradiating at least a portion of at least one of said conveyed plurality of materials with said irradiating light energy and inducing said Raman emission from at least one of the irradiated materials and for collecting reflected light energy from at least one of the irradiated materials;

spectrograph means, coupled to each of said plurality of probe heads, for analyzing each of the resulting plurality of collected reflected light energies to determine their frequency components and outputting data corresponding to said frequency components, recognition processor means, coupled to said spectrograph means, for processing the said data corresponding to the frequency components of each of said plurality of collected reflected light energies to identify at least one of the irradiated materials as a recognized polymer type and to generate a signal to indicate whether at least one of the irradiated materials should be separated, and sorting means, coupled to said recognition processor means, wherein said sorting means separates at least one of said plurality of materials in accordance with said signal.

* * * * *